(12) United States Patent
Neubeck et al.

(10) Patent No.: US 12,344,882 B2
(45) Date of Patent: * Jul. 1, 2025

(54) AUTOMATED BIOCONVERSION PROCESS FOR CONTINUOUS AND AUTOMATIC CONTROL FOR CO BIOCONVERSIONS

(71) Applicant: JUPENG BIO (HK) LIMITED, Hong Kong (CN)

(72) Inventors: Michael Neubeck, Fayetteville, AR (US); Trevor Stilwell, Fayetteville, AR (US); Nestor Camargo, Fayetteville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/532,727

(22) Filed: Dec. 7, 2023

(65) Prior Publication Data

US 2024/0110207 A1     Apr. 4, 2024

Related U.S. Application Data

(63) Continuation of application No. 17/122,366, filed on Dec. 15, 2020, now Pat. No. 11,879,146.

(60) Provisional application No. 62/961,743, filed on Jan. 16, 2020.

(51) Int. Cl.

| | |
|---|---|
| *C12P 7/54* | (2006.01) |
| *C12N 1/20* | (2006.01) |
| *C12P 7/08* | (2006.01) |
| *C12P 7/56* | (2006.01) |
| *C12R 1/145* | (2006.01) |
| *G06F 17/18* | (2006.01) |

(52) U.S. Cl.
CPC ............... *C12P 7/54* (2013.01); *C12P 7/08* (2013.01); *C12P 7/56* (2013.01); *G06F 17/18* (2013.01); *C12N 1/205* (2021.05); *C12R 2001/145* (2021.05)

(58) Field of Classification Search
None
See application file for complete search history.

(56) References Cited

U.S. PATENT DOCUMENTS 11,879,146 B2 *   1/2024   Neubeck ............... C12P 7/54
2016/0281114 A1 *  9/2016   Atiyeh ................. C12P 7/065

FOREIGN PATENT DOCUMENTS

WO     WO-2011002318 A1 *   1/2011   ............ C12M 41/26

OTHER PUBLICATIONS

Fernandez-Delgado et al. J. Mach. Learn. Res. 15 (2014) 3133-3181 (Year: 2014).*

* cited by examiner

*Primary Examiner* — Christian L Fronda
(74) *Attorney, Agent, or Firm* — Mengqi Zheng; James Krueger

(57) ABSTRACT

Control processes are provided for enhancing biological processes for converting gaseous substrates to useful end products such as ethanol. A process includes providing a gaseous substrate comprising one or more of CO and $CO_2$ to a bioreactor at a substrate addition rate. Acetogenic bacteria provided to the bioreactor ferment the gaseous substrate in a fermentation broth. The process includes determining a concentration of carboxylic acids and/or carboxylates in the fermentation broth. A control algorithm uses those concentrations to adjust the gaseous substrate addition rate.

13 Claims, 8 Drawing Sheets

AUTOMATED BIOCONVERSION PROCESS FOR CONTINUOUS AND AUTOMATIC CONTROL FOR CO BIOCONVERSIONS

This application is a continuation application of U.S. application Ser. No. 17/122,366, filed Dec. 15, 2020, which claims the benefit of U.S. Provisional Application No. 62/961,743, filed Jan. 16, 2020, each of which are incorporated in their entirety herein by reference.

A process is provided for bioconversion of gaseous substrates that includes carbon monoxide. More specifically, the process includes controlling bioconversion of gaseous substrates by using a concentration of carboxylic acid and/or carboxylates to control a gaseous substrate addition rate.

BACKGROUND

Carbon monoxide generation occur from natural processes as well as industrial processes that include combustion of fossil fuels such as coal, oil and natural gas. Due in part to industrial processes, carbon emission to the atmosphere continue to increase.

Fermentation controls are often based on manual measurement and adjustments based on results of those measurements. These manual processes have certain amount of lag time between measurement and adjustment which can result in less effective fermentation. Further, the use of more automated control strategy can provide a more accurate control, provide a faster reaction time, and reduce labor costs.

In view of the large amount of carbon monoxide (CO) generated, there is a need for bacterial fermentation systems that can effectively utilize carbon monoxide.

SUMMARY

A process includes providing a gaseous substrate comprising CO to a bioreactor at a substrate addition rate. Acetogenic bacteria provided to the bioreactor ferment the gaseous substrate in a fermentation broth. The process includes determining a concentration of $A_M$ in the fermentation broth, where $A_M$ is a concentration of carboxylic acids and carboxylates. A control algorithm uses $A_M$ to adjust the gaseous substrate addition rate.

BRIEF DESCRIPTION OF FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
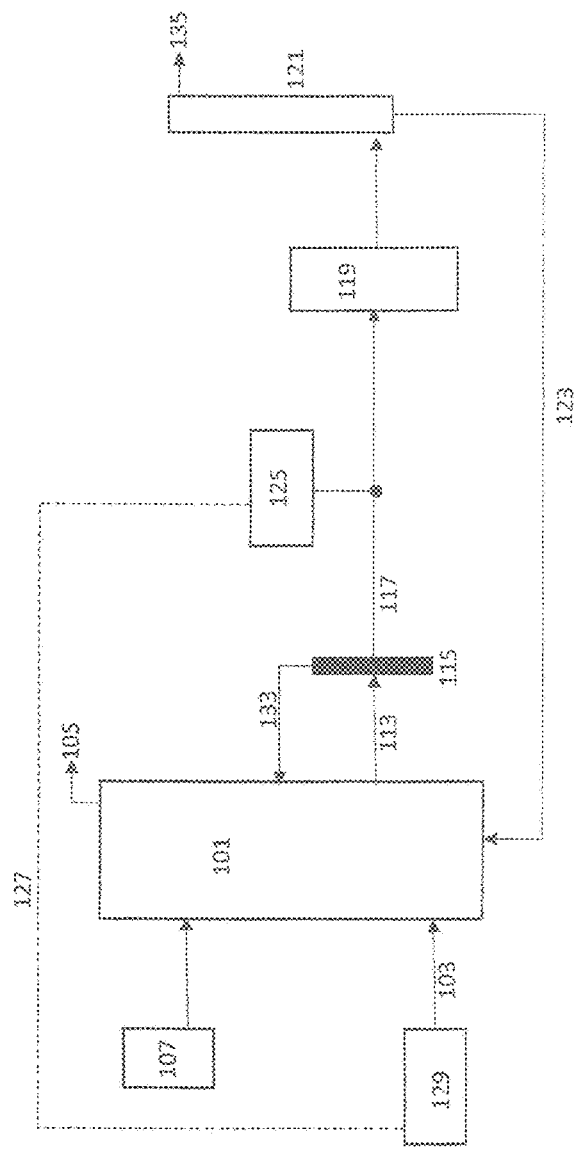
FIG. 1 illustrates a bioreactor system.

The following description is not to be taken in a limiting sense, but is made merely for the purpose of describing the general principles of exemplary embodiments. The scope of the disclosure should be determined with reference to the claims.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "fermentor" includes a fermentation device/bioreactor consisting of one or more vessels and/or towers or piping arrangements, which includes a batch reactor, semi-batch reactor, continuous reactor, continuous stirred tank reactor (CSTR), bubble column reactor, external circulation loop reactor, internal circulation loop reactor, immobilized cell reactor (ICR), trickle bed reactor (TBR), moving bed biofilm reactor (MBBR), gas lift reactor, membrane reactor such as hollow fibre membrane, bioreactor (HFMBR), static mixer, gas lift fermentor, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of CO to carboxylic acid. In another aspect, fermentation refers to conversion of CO to alcohol. In still another aspect, fermentation refers to conversion of CO to alcohol and carboxylic acid.

The term "cell density" means mass of microorganism cells per unit volume of fermentation broth, for example, grams/liter.

As used herein, productivity is expressed as STY. In this aspect, productivity STY (space time yield) may be expressed as alcohol STY, grams Ethanol/(Liter*Day).

As used herein, "oxygenated hydrocarbonaceous compounds" may include carbon, $H_2$ and oxygen containing compounds, such as for example, ethanol and butanol.

In one aspect, the system may include one or more bioreactors configured to receive a gaseous substrate. The one or more bioreactors may include a fermentation broth that includes acetogenic bacteria and a fermentation medium. A fermentation control system may include a sampling apparatus configured to isolate a sample of fermentation broth from the bioreactor, and an analyzer configured to analyze the isolated sample. The system may include a controller configured to control a gaseous substrate addition rate based at least in part on a concentration of carboxylic acid and carboxylated as determined by the analyzer.

Further aspects are directed to computer program products that include non-transitory computer readable media having computer programs embodied thereon. These computer programs include instructions for causing a processor to perform steps needed to carryout the control processes described herein. These processes include receiving information that is input to a controller configured to control gaseous substrate addition rates. The information that is received and input in this manner includes information received from an analyzer configured to analyze a sample from the bioreactor.

Bioreactor Systems for Conversions of Gaseous Substrates

The process may utilize bioreactor systems, such as for example those described in U.S. Ser. Nos. 16/530,481 and 16/530,502, both filed Aug.2, 2019, U.S. Serial No. 13/471,858, filed May 15, 2012, U.S. Serial No. 13/471,827, filed May 15, 2012 and issued on May 22, 2018 as U.S. Pat. No. 9,976,158 and U.S. Ser. No. 13/473,16, filed May 16, 2012 and issued on Nov. 26, 2013 as U.S. Pat. No. 8,592,19, all of which are incorporated herein by reference.

One aspect of a bioreactor system is shown in FIG. 1. The system may include bioreactor 101 being adapted to ferment a gaseous substrate provided by gaseous substrate addition line 103. The system allows off-gas venting from bioreactor 101 through off-gas vent line 105. Bioreactor 101 may be supplied with nutrient from nutrient supply tank 107.

As further illustrated in FIG. 1, fermentation broth may be removed from the bioreactor 101 through fermentation broth draw line 113 and supplied to microfiltration or ultrafiltration 115. At least a portion of cells from microfiltration or ultrafiltration 115 may be returned to bioreactor 101 by cell return line 133. Permeate may be conveyed from microfiltration or ultrafiltration 115 by permeate line 117 to distillation feed tank 119 and then to distillation tower 121. The distillation tower 121 provides distillation product 135 and water (distillation bottoms). Water (distillation bottoms) may be returned to the bioreactor 101 through water return line 123.

In one aspect, permeate from permeate line 117 may be analyzed by an acid control device 125. The acid control device 125 may provide a signal (shown as dotted signal line 127) to a gas flow controller 129.

Gaseous Substrates

Gaseous substrates may include CO. More specifically, gaseous substrates may be a CO-containing substrate, or combinations of CO-containing substrates and $CO_2$ containing substrates.

CO-Containing Substrate: A CO-containing substrate may include any gas that includes CO. In this aspect, a CO-containing gas may include syngas, industrial gases, and mixtures thereof. In a related aspect, a gaseous substrate may include in addition to CO, nitrogen gas ($N_2$), carbon dioxide ($CO_2$), methane gas ($CH_4$), syngas, and combinations thereof.

Syngas may be provided from any known source. In one aspect, syngas may be sourced from gasification of carbonaceous materials. Gasification involves partial combustion of biomass in a restricted supply of oxygen. The resultant gas may include CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

In another aspect, the process has applicability to support the production of alcohol from gaseous substrates such as high volume CO-containing industrial gases. In some aspects, a gas that includes CO is derived from carbon containing waste, for example, industrial waste eases or from the gasification of other wastes. As such, the processes represent effective processes for capturing carbon that would otherwise be exhausted into the environment. Examples of industrial gases include gases produced during ferrous metal products manufacturing, non-ferrous products manufacturing, petroleum refilling processes, gasification of coal, gasification of biomass, electric power production, carbon black production, ammonia production, methanol production, coke manufacturing and gas reforming.

In another aspect, $H_2$ may be supplied from industrial waste gases or from the gasification of other wastes. As such, the processes represent effective processes for capturing $H_2$ that would otherwise be exhausted into the environment. Examples of industrial gases include gases produced during ferrous metal products manufacturing, non-ferrous products manufacturing, petroleum refining processes, gasification of coal, gasification of biomass, electric power production, carbon black production, ammonia production, methanol production and coke manufacturing. Other sources of $H_2$ may include for example, $H_2O$ electrolysis and bio-generated $H_2$.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate includes CO and $H_2$. In this aspect, the CO-containing substrate will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to $CO_2$ storage and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol, production and/or overall carbon capture. In another aspect, the concentration of $H_2$ in the substrate stream may be increased before the stream is passed to the bioreactor.

According to particular aspects of the disclosure, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles and chemical impurities such as cyanide, oxygen, before introducing it to the fermentation. For example, the gaseous substrate may be filtered or scrubbed using known methods.

Acetogenic Bacteria

The process includes conducting fermentations in the fermentation bioreactor with acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. patent application Ser. No. 2007/0276447. Other suitable microorganisms include those of the genus *Moorella*, including *Moorella sp. HUC22-1*, and those of the genus *Carboxydothermus*. Each of these references is incorporated herein by reference. Mixed cultures of two or more microorganisms may be used.

Additional examples of useful acetogenic bacteria include *Acetogenium kivui*, *Acetoanaerobium noterae*, *Alkalibaculum bacchi* CP11 (ATCC BAA-1772), *Blautia producta*, *Butyribacterium methylotrophicum*, *Caldanaerobacter subterraneous*, *Caldanaerobacter subterraneous pacificus*, *Carboxydothermus hydrogenoformans*, *Clostridium aceticum*, *Clostridium acetobutylicum*, *Clostridium acetobutylicum* P262 (DSM 19630 of DSM7 Germany), *Clostridium autoethanogenum* (DSM 19630 of DSMZ Germany), *Clostridium autoethanogenum* (DSM 10061 of DSM7 Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum*, *Clostridium pasteurianum* (DSM 525 of DSMZ Germany), *Clostridium ragsdalei* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina barkeri*, *Moorella thermoacetica*, *Moorella thermoautotrophica*, *Oxobacter pfennigii*, *Peptostreptococcus productus*, *Ruminococcus productus*, *Thermoanaerobacter kivui*, *Clostridium Sticklandii*, and mixtures thereof Fermentation Medium In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In another aspect, concentrations of various medium components for use with acetogenic bacteria are as follows:

| Element | Concentration mg/L | Feed Rate µg/gram cells/min |
|---|---|---|
| $NH_4^+$ | 164-6560 | 41-1640 |
| Fe | 1.7-68 | 0.425-17 |
| Ni | 0.07-2.81 | 0.017-0.702 |
| Co | 0.037-1.49 | 0.009-0.373 |
| Se | 0.027-1.1 | 0.006-0.274 |
| Zn | 0.116-4.64 | 0.198-5.95 |
| W | 0.8-32.1 | 0.26-8.03 |
| K | 39-1573 | 9.83-393.25 |
| Mg | 1.4-57.3 | 0.35-14.32 |
| S | 15-625 | 3.9-156.2 |
| P | 15-601 | 3.76-150.43 |
| d-biotin | 0.016-0.64 | 0.004-0.16 |
| thiamine HCl | 0.04-1.6 | 0.01-0.4 |
| calcium-D-pantothenate | 0.02-0.81 | 0.005-0.202 |

In one aspect, the medium includes less than about 0.01 g/L yeast extract and less than about 0.01 g/L carbohydrates.

Fermentation Control

Control methodologies, which may be automated, can enhance biological processes for converting gaseous substrates to useful end products such as ethanol. For example, productivities can be increased 300% or more using automated control strategies as compared to processes where automated control strategies are not used.

Figure 2:
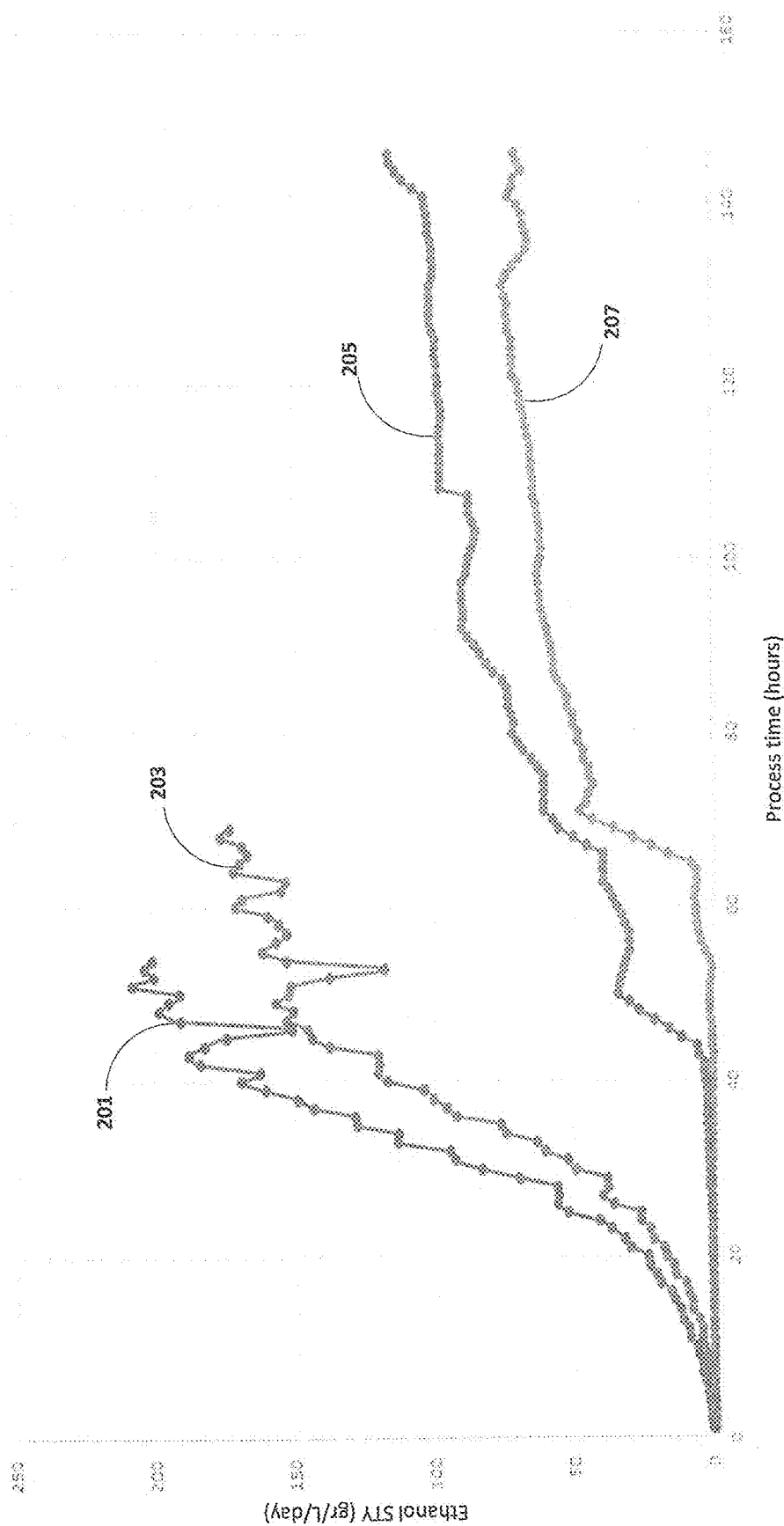
FIG. 2 graphically compares ethanol STY values in an automated control process versus a non-automated control process.

Fermentations conducted in bioreactors with medium and acetogenic bacteria as described herein using the fermentation control methodologies described herein are effective for providing a STY (space time yield) of at least about 100 g ethanol/(L·day). Possible STY values include about 100 g ethanol/(L·day) to about 300 g ethanol/(L·day), in another aspect, about 100 g ethanol/(L·day) to about 250 g ethanol/(L·day), and in another aspect, about 100 g ethanol/(L·day) to about 200 g ethanol/(L·day). A comparison of STY values using an automated control system (shown as 201 and 203) as described herein versus a manual control system (shown as 205 and 207) is shown in FIG. 2. In another aspect shown in FIG. 2, automated control systems were able to increase STY much faster than manual systems. In this aspect, determining a concentration of $A_M$ in the fermentation broth and using $A_M$ in a control algorithm to adjust the gaseous substrate addition rate is accomplished in less than 30 minutes, in another aspect, about 0.1 seconds to about 30 minutes, in another aspect, about 0.1 seconds to about 20 minutes, in another aspect, about 0.21 seconds to about 10 minutes, in another aspect, about 0.1 seconds to about 1 minute, and in another aspect, about 1 second to about 5 minutes.

Figure 3:
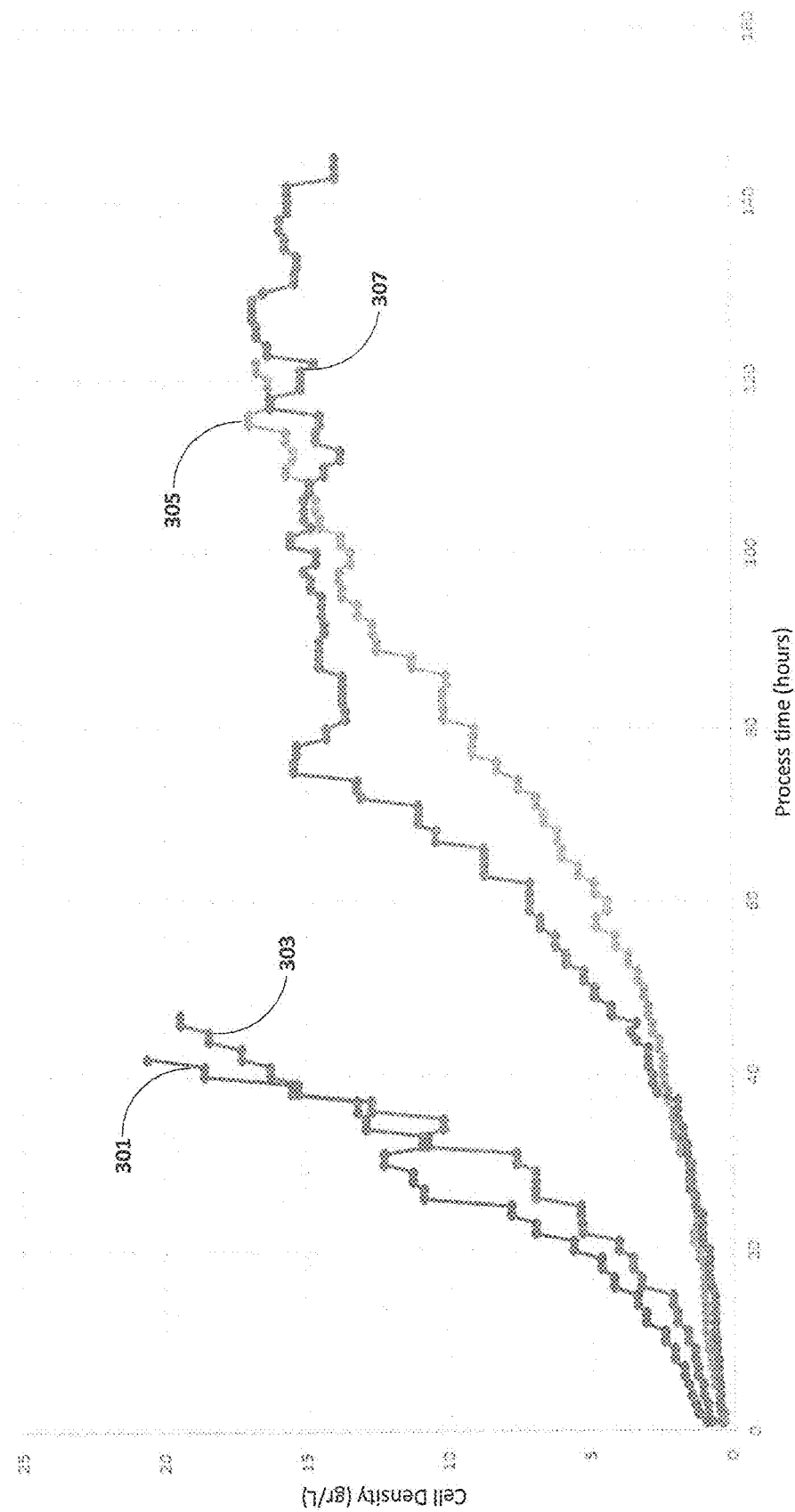
FIG. 3 graphically compares cell density values in an automated control process versus a non-automated control process.

Fermentations conducted in bioreactors with medium and acetogenic bacteria as described herein using the fermentation control methodologies described herein are effective for providing a cell density of at least about 1 gram/liter, in another aspect about 1 to about 50 grams/liter, and in another aspect about 3 to about 30 grams/liter. A comparison of cell density values using automated an automated control system (shown as 301 and 303) as described herein versus a manual control system (shown as 305 and 307) is shown in FIG. 3. In another aspect shown in FIG. 3, automated control systems were able to increase cell density much faster than manual systems.

Process control methodologies are described in FIGS. 4-8. Various control aspects are shown in these Figures. The various control aspects may be combined in any manner to provide an overall process control methodology.

Figure 4:
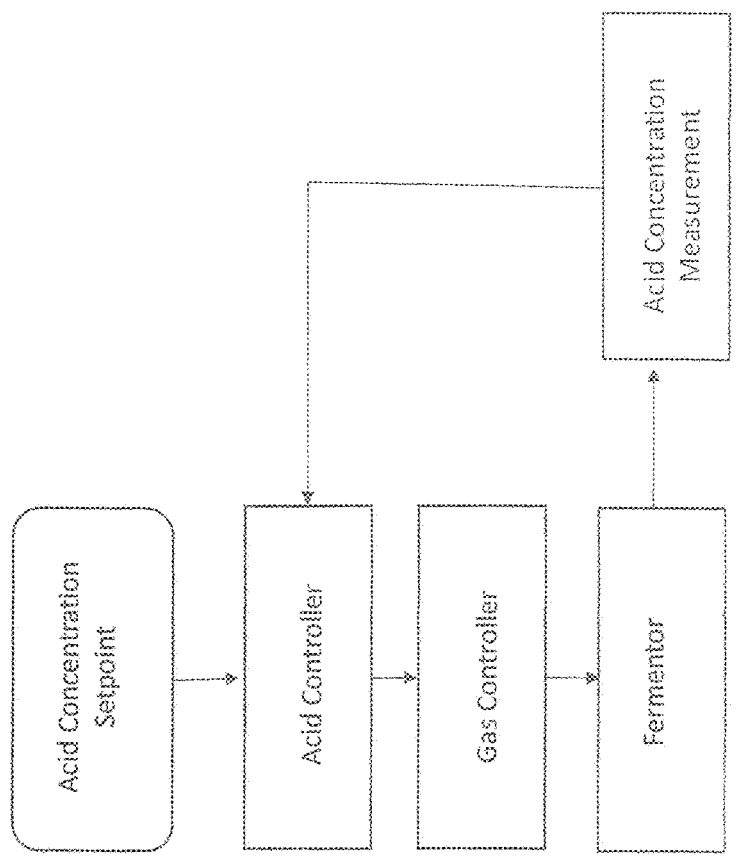
FIG. 4 is a flow chart providing a general overview of a process control methodology

A general overview of a process control methodology is shown in FIG. 4. In this aspect, the process includes providing a gaseous substrate that includes one or more of CO and $CO_2$ to a bioreactor at a gaseous substrate addition rate. Acetogenic bacteria in the bioreactor ferment the gaseous substrate in a fermentation broth. The process includes using an acid concentration measurement to determine an acid concentration in the fermentation broth from the fermentor. The gas controller adjusts the gaseous substrate addition rate to reach an acid concentration target range. The acid concentration measured is a concentration of carboxylic acids, carboxylates or a combination of carboxylic acids and carboxylates. A fermentation broth may be utilized directly for acid measurements. In another aspect, a permeate may be formed from the fermentation broth and the acid concentration in the permeate may be determined. Measurements of acid concentration may be conducted using any of the analytical techniques described herein.

Figure 5:
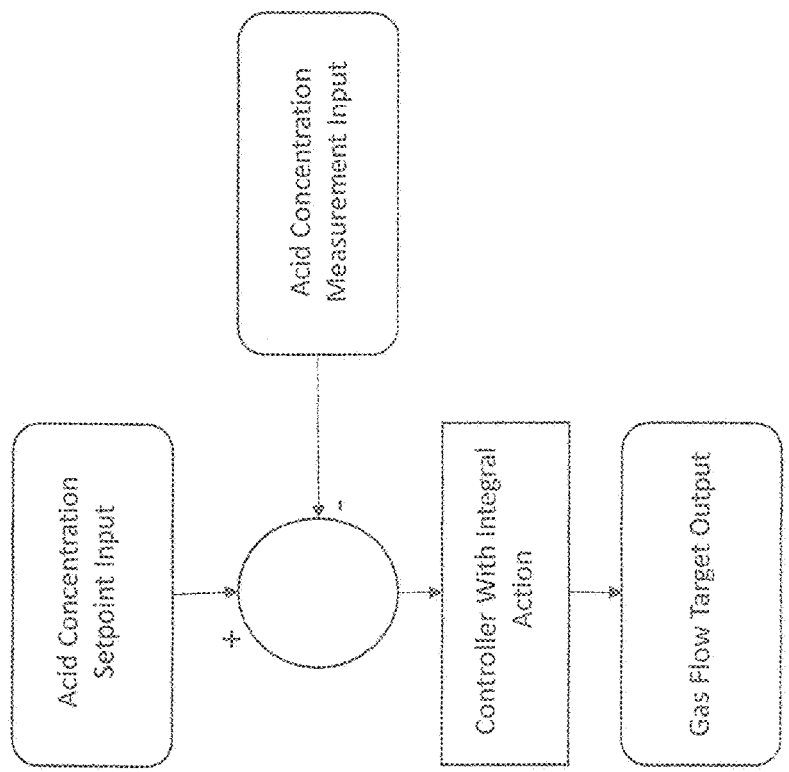
FIG. 5 is a flow chart describing a process control methodology for acid controllers.

Another aspect of a process control methodology for acid controllers is shown in FIG. 5. In this aspect, controller inputs include an acid concentration setpoint and an acid concentration measurement. Inputs may be used in control algorithms provided by a controller with integral action. The controller provides a gas flow target output.

Figure 6:
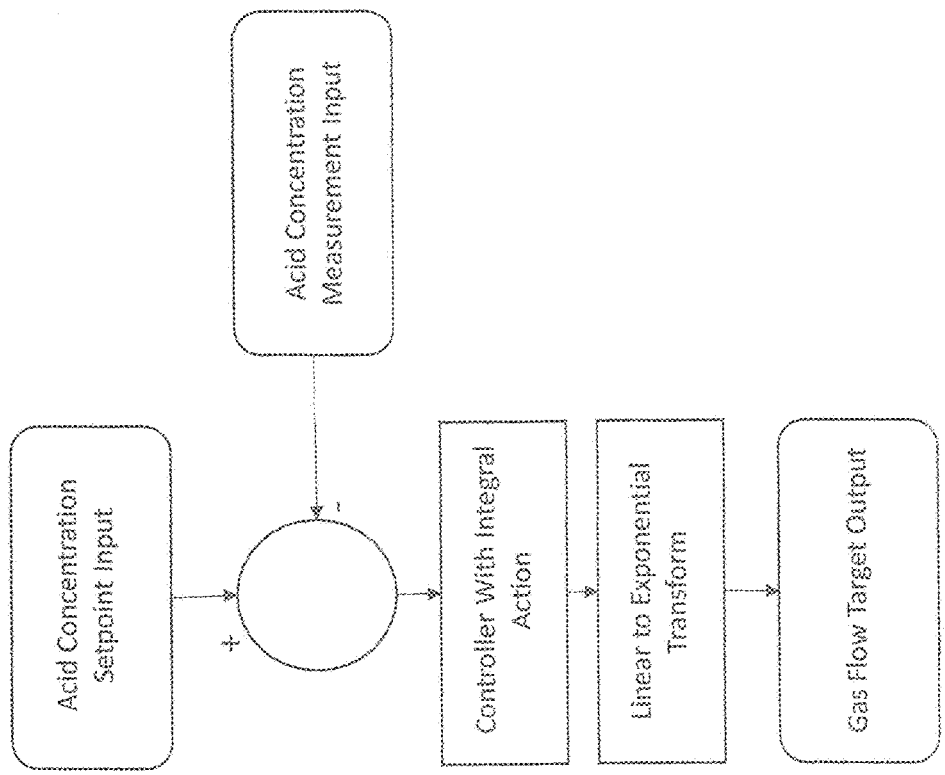
FIG. 6 is a flow chart describing another aspect of a process control methodology for acid controllers

Another aspect of a process control methodology for acid controllers is shown in FIG. 6. In this aspect, controller inputs include an acid concentration setpoint and an acid concentration measurement. Inputs may be used in control algorithms provided by a controller with integral action. Linear to exponential transformation may be applied to provide a gas flow target output.

Figure 7:
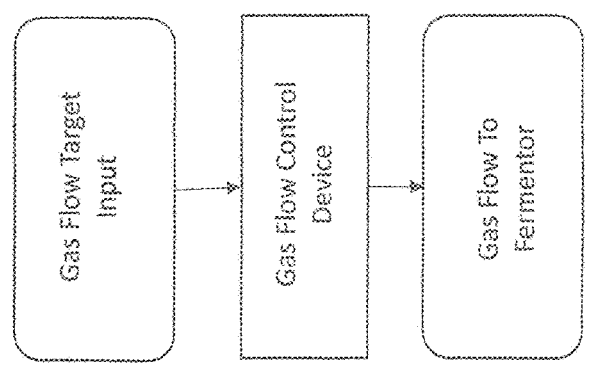
FIG. 7 is a flow chart describing a process control methodology for gas flow controllers.

Another aspect of a process control methodology for gas controllers is shown in FIG. 7. In this aspect, a gas flow target input is provided to a gas flow control device. The gas flow control device controls gas flow to the fermentor.

Figure 8:
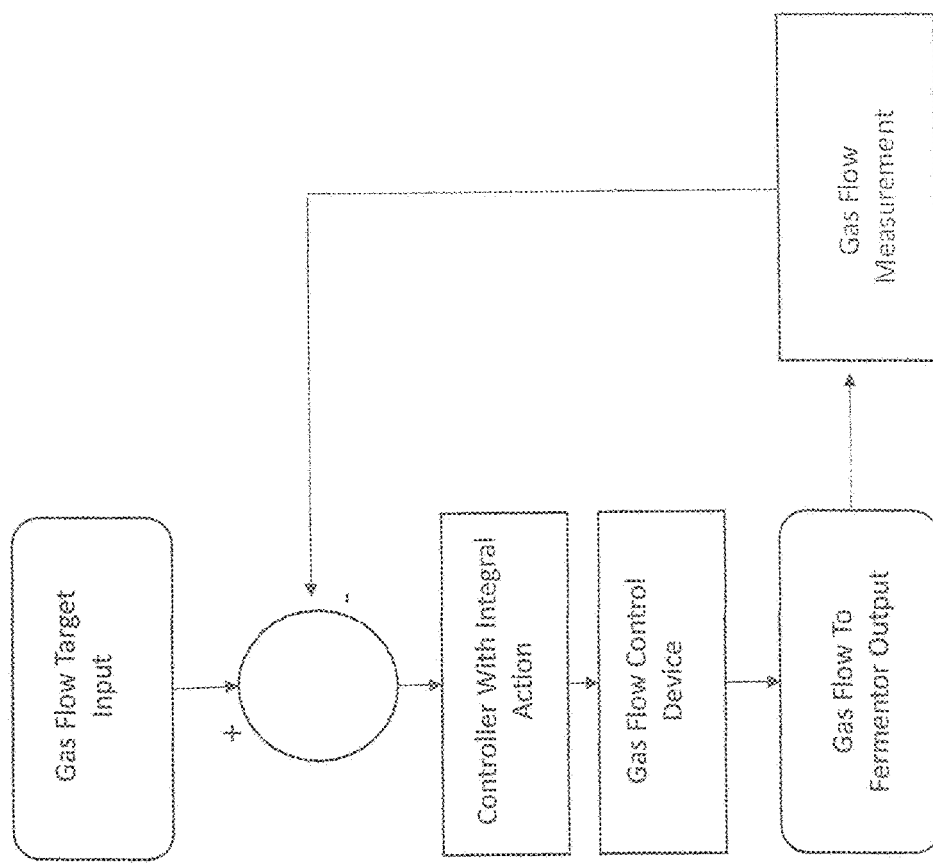
FIG. 8 is a flow chart describing another aspect of a process control methodology for gas flow controllers.

Another aspect of a process control methodology for gas controllers is shown in FIG. 8. In this aspect, controller inputs include a gas flow target input and a gas flow measurement. Inputs may be used in control algorithms provided by a controller with integral action. The controller operates to control a gas flow control device. The gas flow control device provides a gas flow to fermentor output.

Sampling: Fermentation broth may be withdrawn directly from the bioreactor. A sample line from a bleed stream or other stream for withdrawing fermentation broth may be fluidly connected to a suitable analytical device for on-line measurement. Sampling systems for online analysis from one or multiple reactors may include suitable conduits (e.g., tubing or piping) valves, pumps, and actuators to allow the automated sampling of a desired bioreactor at a desired time, and suitable devices for flushing (purging) sample lines.

In one aspect, the process includes conducting analysis on a permeate which is free or substantially free of bacterial cells as a result of filtration or membrane separation. A permeate stream may be available from a cell separation system and that permeate stream may be used for analysis. Sample conditioning means, such as carbon filtration, temperature control, bubble removal and combinations of one or more sample conditioning means, may be utilized.

Fermentation broth may be measured continuously or intermittently, for example periodically, with the period of time between each successive measurement being generally from 0.1 seconds to 10 minutes, in one aspect, from 0.1 seconds to 5 minutes, in one aspect, every 0.1 seconds to every 120 seconds, in one aspect, every 0.5 seconds to every 60 seconds, and in another aspect, every second to every 10 seconds.

Measurement of carboxylic acid and carboxylates: In one aspect, the process includes determining a concentration of $A_M$ in the fermentation broth, where $A_M$ is a concentration of carboxylic acids and carboxylates. The process includes determining the concentration of carboxylic acids and carboxylates using an analytical device selected from the group consisting of near infrared spectroscopy (NIR), gas chromatography, high pressure liquid chromatography, mass spectroscopy and combination thereof. In one aspect, NIR measures carboxylic acid and/or carboxylates in the permeate. The NIR may be in-line, which allows for continuous measurements. Useful NIR frequencies may include in one aspect, about 800 to 2200 nm, in another aspect, about 1280 to about 2184 nm, in another aspect, about 1640 to about 1724 nm, in another aspect, about 1630 to about 1910 nm, and in another aspect, about 870 to about 2184 nm.

Control Algorithms: In one aspect, control methodologies as described herein are automated, involving the use of a computer program with appropriate instructions for causing a processor to transmit the necessary signal to controller for carrying out those control methodologies.

In one aspect, $A_M$ values provided by measurement of carboxylic acid and carboxylates are used in a control algorithm to adjust a substrate addition rate. In this aspect, the control algorithm includes determining an $I_{term}$ according to a formula. $I_{term}=E_{int}/I$, wherein I is a constant, wherein $E_{int}=(\text{previous } E_{int})+(A_M-A_T)*dt$, wherein dt is a time interval between determining $A_M$ in the permeate, wherein previous $E_{int}$ and $E_{int}$ are values at a beginning and end or time interval dt. The control algorithm may further include determining a $P_{term}$ according to a formula $P_{term}=(A_M-A_T)*P$, wherein $A_T$ is a target concentration of carboxylic acid and carboxylates, and P is a constant. In addition, the control algorithm further includes determining $E_{int}$ according to a formula $E_{int}$=(previous $E_{int}$)+$(A_M-A_T)$*dt, wherein dt is a time, interval between determining $A_M$ in the permeate, wherein previous $E_{int}$ and $E_{int}$ are values at a beginning and end or time interval dt; determining $I_{term}$ according to a formula $I_{term}$=$E_{int}$/I, wherein I is a constant; and determining a Controller$_{output}$ according to a formula Controller$_{output}$=P$_{term}$+I$_{term}$. I and P constants are decided base on process conditions and/or equipment. In this aspect, P may be 0 to 50, in another aspect, about 1 to about 30, and in another aspect, about 3 to about 10. I may be about 100 to about 10,000, in another aspect, about 500 to about 5000, and in another aspect, about 800 to about 2500. Values and ranges of the controller tuning constants, I and P, are appropriate subject to the following qualifications: time increment ("dt") in units of seconds; acid measurement (and acid error) in units of g/L total acid; controller output is then exponentialized such that controller output linear span from 0 to 100 will map onto a GFR exponential span from ~10% of initial GFR required at inoculation conditions (of ~1 g/L cell concentration) to about 150% of GFR required at high productivity steady state. Use of different time units (e.g. minutes), acid measurement units (e.g. ppm), or exponentialization spans would result in different appropriate values and ranges of the controller tuning constants and exponential constant.

Controllers utilized in the system may include I controllers, PI controllers, ID controllers, and PID controllers.

During the fermentation control, the pH of the fermentation broth is maintained within a range. For example, in one aspect, the pH is maintained between about 4 to about 6.9, in another aspect, about 5 to about 6.5, in another aspect about 5.1 to about 6, in another aspect, about 5.2 to about 6, in another aspect, about 4.5 to about 5, in another aspect, about 4 to about 4.5, in another aspect, about 4.75 to about 4.9, in another aspect about 4.6 to about 4.75, in another aspect, about 4.45 to about 4.6, in another aspect, about 4.3 to about 4.45, in another aspect, about 4.6 to about 4.9, in another aspect, about 4.45 to about 4.75, and in still another aspect, about 4.3 to about 4.6.

EXAMPLES

Example 1: Control Calculations

A fermentation was conducted using *Clostridium ljungdahlii* C-01 (ATCC 55988). Acid in a permeate stream was measured using NIR. The Table below sets forth control calculations over several iterations. As shown, when acid concentration increases, the controller precisely increases the gas flow rate. Alternatively, when acid concentration decreases, the controller precisely decreases the gas flow rate

| Time hh:mm time | Acid measured g/L $A_M$ | Acid target g/L $A_T$ | Error value g/L E_val | Proportional term % P_term | Error integral g/L · s E_int | Integral term % I_term | PID output % PID_out | Gas flowrate L/min GFR | Mode Auto or Cas Mode | |
|---|---|---|---|---|---|---|---|---|---|---|
| 7:00 | | | | | | | | 16.50 | | Initial integral for |
| 7:01 | 2.60 | 2.50 | 0.10 | 0.50 | 46193 | 44.61 | 45.11 | 16.50 | Auto | bumpless transfer |
| 7:02 | 2.63 | 2.50 | 0.13 | 0.63 | 46200 | 44.62 | 45.24 | 16.64 | Cas | Acid above target |
| 7:03 | 2.65 | 2.50 | 0.15 | 0.75 | 46209 | 44.63 | 45.38 | 16.77 | Cas | and rising |
| 7:04 | 2.68 | 2.50 | 0.18 | 0.87 | 46220 | 44.64 | 45.51 | 16.92 | Cas | -- |
| 7:05 | 2.70 | 2.50 | 0.20 | 1.00 | 46232 | 44.65 | 45.65 | 17.06 | Cas | P and I both |
| 7:06 | 2.73 | 2.50 | 0.23 | 1.13 | 46245 | 44.66 | 45.78 | 17.21 | Cas | contribute to |
| 7:07 | 2.75 | 2.50 | 0.25 | 1.25 | 46260 | 44.67 | 45.92 | 17.36 | Cas | increase GFR |
| 7:08 | 2.78 | 2.50 | 0.27 | 1.38 | 46277 | 44.69 | 46.07 | 17.51 | Cas | |
| 7:09 | 2.80 | 2.50 | 0.30 | 1.50 | 46295 | 44.71 | 46.21 | 17.67 | Cas | |
| 7:10 | 2.83 | 2.50 | 0.32 | 1.63 | 46314 | 44.73 | 46.35 | 17.82 | Cas | |
| 7:11 | 2.83 | 2.50 | 0.32 | 1.63 | 46334 | 44.75 | 46.37 | 17.85 | Cas | Acid above target |
| 7:12 | 2.83 | 2.50 | 0.32 | 1.63 | 46353 | 44.76 | 46.39 | 17.87 | Cas | and flat |
| 7:13 | 2.83 | 2.50 | 0.32 | 1.63 | 46373 | 44.78 | 46.41 | 17.89 | Cas | -- |
| 7:14 | 2.83 | 2.50 | 0.32 | 1.63 | 46392 | 44.80 | 46.43 | 17.91 | Cas | P constant; I |
| 7:15 | 2.83 | 2.50 | 0.32 | 1.63 | 46412 | 44.82 | 46.45 | 17.93 | Cas | increasing GFR |
| 7:16 | 2.83 | 2.50 | 0.32 | 1.63 | 46431 | 44.84 | 46.46 | 17.95 | Cas | slowly |
| 7:17 | 2.83 | 2.50 | 0.32 | 1.63 | 46451 | 44.86 | 46.48 | 17.97 | Cas | |
| 7:18 | 2.83 | 2.50 | 0.32 | 1.63 | 46470 | 44.88 | 46.50 | 17.99 | Cas | |
| 7:19 | 2.83 | 2.50 | 0.32 | 1.63 | 46490 | 44.90 | 46.52 | 18.01 | Cas | |
| 7:20 | 2.83 | 2.50 | 0.32 | 1.63 | 46509 | 44.91 | 46.54 | 18.03 | Cas | |
| 7:21 | 2.81 | 2.50 | 0.31 | 1.55 | 46528 | 44.93 | 46.48 | 17.97 | Cas | Acid above target |
| 7:22 | 2.80 | 2.50 | 0.29 | 1.48 | 46546 | 44.95 | 46.42 | 17.91 | Cas | but falling |
| 7:23 | 2.78 | 2.50 | 0.28 | 1.40 | 46562 | 44.97 | 46.37 | 17.84 | Cas | -- |
| 7:24 | 2.77 | 2.50 | 0.26 | 1.32 | 46578 | 44.98 | 46.31 | 17.77 | Cas | GFR decreasing as |
| 7:25 | 2.75 | 2.50 | 0.25 | 1.25 | 46593 | 45.00 | 46.25 | 17.71 | Cas | decreasing P |
| 7:26 | 2.74 | 2.50 | 0.23 | 1.17 | 46607 | 45.01 | 46.18 | 17.64 | Cas | counteracts |
| 7:27 | 2.72 | 2.50 | 0.22 | 1.10 | 46621 | 45.02 | 46.12 | 17.57 | Cas | increasing I |
| 7:28 | 2.71 | 2.50 | 0.20 | 1.02 | 46633 | 45.03 | 46.06 | 17.50 | Cas | |
| 7:29 | 2.69 | 2.50 | 0.19 | 0.95 | 46644 | 45.05 | 46.00 | 17.43 | Cas | |
| 7:30 | 2.68 | 2.50 | 0.17 | 0.87 | 46655 | 45.06 | 45.93 | 17.36 | Cas | |
| 7:31 | 2.66 | 2.50 | 0.16 | 0.80 | 46664 | 45.06 | 45.86 | 17.29 | Cas | | dt = 60, P_const = 5, I_cont = 1036, exp_const = 0.062146
Error value = $A_M - A_T$
Proportional term = P_const * E_val
Error integral = IF(Mode = "Cas", (previous E_int) + E_val * dt, (LN(previous GFR)/exp_const − P_term) * I_const)
Integral term = E_int/I_const
PID output = P_term + I_term
Gas Flowrate = IF(Mode = "Cas", EXP(exp_const * PID_out), previous GFR)
Acid target ($A_T$) = 2.5 g/L While the disclosure herein disclosed has been described by means of specific embodiments, examples and applications thereof, numerous modifications and variations could be made thereto by those skilled in the art without departing from the scope of the disclosure set forth in the claims.

What is claimed is:

1. An automated bioconversion process comprising:
providing a gaseous substrate comprising CO to a bioreactor at a substrate addition rate;
providing acetogenic bacteria to the bioreactor;
fermenting the gaseous substrate in a fermentation broth;
continuously measuring a concentration of $A_M$ in the fermentation broth, where $A_M$ is a concentration of carboxylic acids and carboxylates; and
automatically adjusting the gaseous substrate addition rate through one or more controllers, wherein a computer program uses the $A_M$ in a control algorithm to cause a processor to transmit control signals to the one or more controllers.

2. The process according to claim 1 wherein the control algorithm further comprises determining an $I_{term}$ according to a formula $I_{term}=E_{int}/I$, wherein I is a constant;
wherein $E_{int}=$(previous $E_{int}$)+$(A_M-A_T)$*dt, wherein dt is a time interval between determining $A_M$ in the permeate, wherein previous $E_{int}$ and $E_{int}$ are values at a beginning and end or time interval dt.

3. The process according to claim 2 wherein I=100 to 10,000.

4. The process according to claim 1 wherein a permeate is formed from the fermentation broth and the concentration of carboxylic acid and carboxylates is measured in the permeate.

5. The process of claim 1 wherein the concentration of carboxylic acid and carboxylates is measured by an analytical technique selected from the group consisting of near infrared spectroscopy (NIR), gas chromatography, high pressure liquid chromatography, mass spectroscopy and combination thereof.

6. The process of claim 1 wherein the process provides an STY of at least about 100 g ethanol/(L·day).

7. The process of claim 1 wherein determining the concentration of $A_M$ in the fermentation broth and using $A_M$ in the control algorithm to adjust the gaseous substrate addition rate is accomplished in less than 30 minutes.

8. The process of claim 1 wherein the acetogenic bacteria is selected from a group consisting of *Clostridium bacteria, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), Clostridium ragsdalei P11 (ATCC BAA-622), *Clostridium scatologenes, Clostridium thermoaceticum, Clostridium ultunense,* acetogenic bacteria, *Acetobacterium bacteria, Acetogenium kivui, Acetoanaerobium noterae, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Desulfotomaculum kuznetsovii, Eubacterium limosum, Geobacter sulfurreducens, Methanosarcina acetivorans, Methanosarcina barkeri, Moorella thermoacetica, Moorella thermoautotrophica, Oxobacter pfennigii, Peptostreptococcus productus, Ruminococcus productus, Thermoanaerobacter kivui, Clostridium Stick-landii* and combinations thereof.

9. The process according to claim 2 wherein the control algorithm comprises determining the $P_{term}$ according to a formula $P_{term}=(A_M-A_T)$*P, wherein $A_T$ is a target concentration of carboxylic acid and carboxylates, and P is a constant.

10. The process according to claim 9 wherein P=0 to 50.

11. The process according to claim 2 wherein the control algorithm further comprises determining $E_{int}$ according to a formula $E_{int}=$(previous $E_{int}$)+$(A_M-A_T)$*dt, wherein dt is a time interval between determining $A_M$ in the permeate, wherein previous $E_{int}$ and $E_{int}$ are values at a beginning and end or time interval dt;
determining $I_{term}$ according to a formula $I_{term}=E_{int}/I$, wherein I is a constant; and
determining a $Controller_{output}$ according to a formula $Controller_{output}=P_{term}+I_{term}$.

12. The process of claim 1 wherein the process maintains a pH in a range of about 4 to about 6.9.

13. The process of claim 1 wherein the one or more controllers is selected from the group consisting of I controller, PI controller, ID controller, PID controller and combinations thereof.

* * * * *